(12) United States Patent
Mitsuhashi et al.

(10) Patent No.: US 7,816,081 B2
(45) Date of Patent: Oct. 19, 2010

(54) METHOD OF MINIMIZING REAGENT CONSUMPTION IN MICROPLATE-BASED REACTIONS

(75) Inventors: Masato Mitsuhashi, Irvine, CA (US); Mieko Ogura, Newport Coast, CA (US)

(73) Assignees: Hitachi Chemical Co., Ltd., Tokyo (JP); Hitachi Chemical Research Center, Inc., Irvine, CA (US)

( * ) Notice: Subject to any disclaimer, the term of this patent is extended or adjusted under 35 U.S.C. 154(b) by 184 days.

(21) Appl. No.: 11/913,052

(22) PCT Filed: Apr. 28, 2006

(86) PCT No.: PCT/US2006/016321

§ 371 (c)(1),
(2), (4) Date: Jan. 30, 2008

(87) PCT Pub. No.: WO2006/116708

PCT Pub. Date: Nov. 2, 2006

(65) Prior Publication Data

US 2009/0263837 A1    Oct. 22, 2009

(51) Int. Cl.
*C12Q 1/68* (2006.01)

(52) U.S. Cl. .......................... 435/6; 435/7.9; 436/518; 436/809

(58) Field of Classification Search ............... None
See application file for complete search history.

(56) References Cited

U.S. PATENT DOCUMENTS

| 4,276,259 A | 6/1981 | Eibl et al. |
| 4,891,321 A | 1/1990 | Hubscher |
| 4,956,150 A * | 9/1990 | Henry .................. 422/102 |
| 6,383,802 B1 | 5/2002 | Bertling |

FOREIGN PATENT DOCUMENTS

| DE | 33 36 738 A1 | 5/1985 |
| DE | 19826153 A1 | 12/1998 |
| EP | 0245994 A2 | 4/1987 |

(Continued)

OTHER PUBLICATIONS

Brehm et al., Rapid Production of TNT-◻ following TCR Engagement of Naive CD8 T Cells, The Journal of Immunology, 2005, vol. 175, pp. 5043-5049.

(Continued)

*Primary Examiner*—Christopher L Chin
(74) *Attorney, Agent, or Firm*—Knobbe, Martens, Olson & Bear LLP

(57) ABSTRACT

A method is provided for performing a reaction, such as the synthesis of concentrated cDNA, in the wells of a microplate while minimizing the volume of the solution of reagents required to perform the reaction. In the method, a pestle is inserted into the well of a microplate to which a substance has been immobilized. A volume of reagent solution is introduced into the well that is insufficient to cover the portion of the well onto which the substance is immobilized. The insertion of the pestle displaces reagent solution and increases the surface area of the solution in contact with the portion of the well to which the substance has been immobilized when the pestle is inserted.

14 Claims, 3 Drawing Sheets

FOREIGN PATENT DOCUMENTS

WO      WO 99/032654 A1     12/1998

OTHER PUBLICATIONS

Debets et al., Fc-Receptor Cross-Linking Induces Rapid Secretion of Tumor Necrosis Factor (Cachectin) by Human Peripheral Blood Monocytes, The Journal of Immunology, Aug. 15, 1998, vol. 141, Issue 4, pp. 1197-1201.

Dunkley et al., A Modified Cr Release Assay for Cytotoxic Lymphocytes, Journal of Immunological Methods, 1974, vol. 6, pp. 39-51.

Esser, Alfred F, The membrane attack complex of complement. Assembly, structure and cytotoxic activity, Toxicology, 1994, vol. 87, pp. 229-247, Ireland.

Garcia et al., How the T Cell Receptor Sees Antigen- A Structural View, Cell, Minireview, Aug. 12, 2005, vol. 122, pp. 333-336.

Hamaguchi, Y et al., Direct reverse transcription-PCR on oligo(dT)-immobilized polypropylene microplates after capturing total mRNA from crude cell lysates, Clinical Chemistry, 1998, vol. 44, Issue 11, pp. 2256-2263.

Kruger-Krasagakes et al., A rapid and sensitive fluorometric microassay for determining cell mediated cytotoxicity to adherent growing cell lines, Journal of Immunological Methods, 1992, vol. 156, pp. 1-8.

Micheau et al., Induction of TNF Receptor I-Mediated Apoptosis via Two Sequential Signaling Complexes, Cell Press, Jul. 25, 2003, vol. 114, pp. 181-190.

\* cited by examiner

US 7,816,081 B2

METHOD OF MINIMIZING REAGENT CONSUMPTION IN MICROPLATE-BASED REACTIONS

BACKGROUND OF THE INVENTION

1. Field of the Invention

The present invention relates to a method for performing a reaction, such as the synthesis of concentrated cDNA, in the wells of a microplate while minimizing the volume of the solution of reagents required to perform the reaction.

2. Description of the Related Art

Plastic microplates have become an indispensable tool in biological and chemical research and development. These microplates feature a plurality of wells (in the standard format, there are 96 wells per microplate) in which separate reactions can take place. They are particularly useful in performing processes requiring the immobilization of substances on a surface (the walls of each well), followed by reaction of the immobilized substances with a reagent or reagents, and rapid assessment of the results in the various wells of the microplate. Depending on the composition of the microplate, there are various substances that can be immobilized to the microplate wells. These include, for example, long oligonucleotides and cDNAs, amino modified oligonucleotides, amino modified cDNAs, proteins, carbohydrates, cells, lysates, tissues, and chemical subunits such as monomers. Microplates to which such substances have been immobilized may be used, for example, in gene expression microarrays, SNP detection microarrays, and protein microarrays, among other applications.

The wells of these microplates have various shapes: some have flat bottoms, while others have rounded bottoms or v-shaped bottoms, leading to a conical well. Typical working volumes of the wells are 75-250 µl. In order to conduct reactions in these wells, it is presently necessary to transfer an amount of reagents to the wells sufficient to cover the surfaces of the wells to which the substances are immobilized. However, these reagents are often quite expensive: for example, polymerase chain reaction enzymes such as reverse transcriptase and RNAsin can cost as much as $7 per reaction in the amounts conventionally required. It would accordingly be desirable to economize on the use of such reagents in conducting the biological reactions.

Furthermore, the development of a standard amount of a reaction product while using a smaller volume of reagents can result in a more concentrated solution of reaction product. This can be important when the resulting solution is assayed for the presence of the reaction product (via fluorescence assay or the like), as the higher concentration of reaction product will lead to a stronger signal.

SUMMARY OF THE INVENTION

In an embodiment of the invention, a method of conducting a reaction in the wells of a microplate having a substance participating in the reaction immobilized onto a portion of a well thereof is provided, the method comprising: transferring a volume of a solution of reagents for the reaction into the well, the volume being insufficient to cover the portion of the well onto which the substance is immobilized; inserting a pestle into the well, thereby increasing the surface area of the solution of reagents in contact with the portion of the well onto which the substance is immobilized; and conducting the reaction.

In a further aspect, the portion of the well onto which the substance is immobilized corresponds to more than half of the surface of the well.

In a further aspect, the portion of the well onto which the substance is immobilized corresponds to the portion covered when approximately 80 µl of reagents are transferred to the well.

In a further aspect, the volume of the solution of reagents is 30 µl or less.

In a further aspect, the substance is an oligonucleotide.

In a further aspect, the oligonucleotide is oligo d(T).

In a further aspect, the substance is an antigen.

In a further aspect, the reaction is a cDNA synthesis reaction.

In a further aspect, the reagents comprise a detergent.

In a further aspect, the detergent is Tween 20.

In a further aspect, the reaction is part of an enzyme-linked immunosorbent assay.

In a further aspect, the reaction is a solid-phase chemical synthesis reaction.

In an embodiment of the invention, a method of synthesizing cDNA is provided, comprising: transferring a mRNA-containing solution to a well of a microplate, at least a portion of said well having oligo d(T) immobilized thereto; hybridizing the mRNA to the oligo d(T); washing the well to remove unbound mRNA; transferring a volume of a solution of reagents for synthesizing cDNA into the well, the volume being insufficient to cover the portion of the well onto which the oligo d(T) is immobilized; inserting a pestle into the well, thereby increasing the surface area of the solution of reagents in contact with the portion of the well onto which the oligo d(T) is immobilized; and conducting a cDNA polymerization reaction.

In a further aspect, the hybridizing step includes inserting a pestle into the well, so as to increase the surface area of the mRNA-containing solution in contact with the portion of the well onto which the oligo d(T) is immobilized.

DETAILED DESCRIPTION OF THE PREFERRED EMBODIMENT

Figure 1:
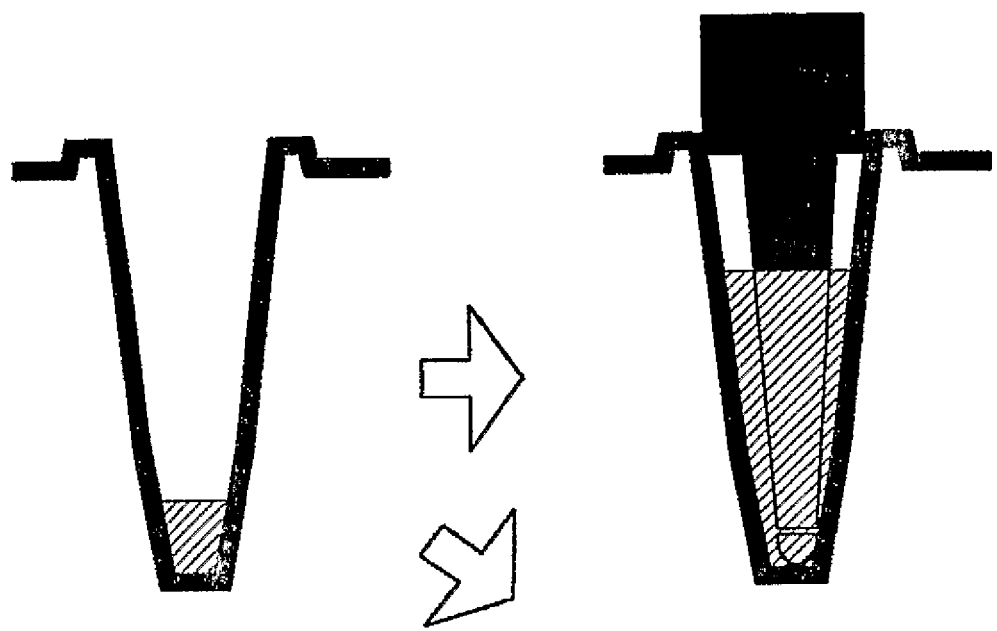
FIG. 1 shows a schematic view of the well of a microplate with a pestle inserted, in accordance with an embodiment of the present invention.
Figure 1:
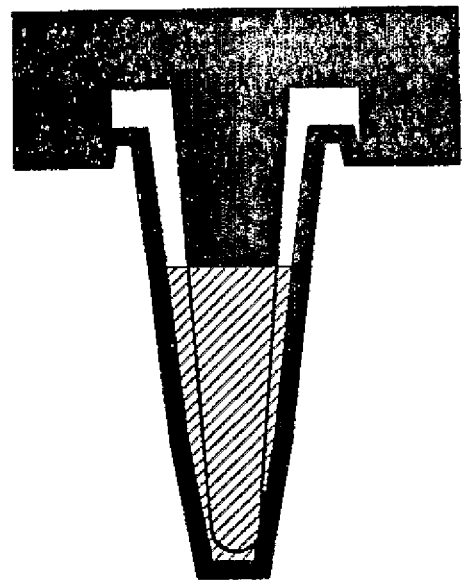

The method of the present invention involves the use of a pestle that is inserted into the well of a microplate to which a substance has been immobilized. A volume of reagent solution is introduced into the well that is insufficient to cover the portion of the well onto which the substance is immobilized. The insertion of the pestle displaces reagent solution and increases the surface area of the solution in contact with the portion of the well to which the substance has been immobilized when the pestle is inserted. In a preferred embodiment, the substance is immobilized to the area of the well that would be covered by 80 µL of liquid (the "80 µL area"), and the amount of reagent solution employed is 30 µL or less. The reaction is conducted with the pestle in place in the well, so that the entirety of the immobilized substance comes into contact with the reagent solution and is thus available to participate in the reaction. After the reaction is terminated or goes to completion, the reaction solution may be subjected to further processing, such as assays for the presence of the reaction product.

The present method may be employed in any solid-phase reaction. Examples of such solid phase reactions include, for example, cDNA synthesis via polymerase chain reaction using mRNA captured by oligo d(T) molecules immobilized on the wells; enzyme-linked immunosorbent assay (ELISA) in which an antigen is immobilized on the well surface, and is then exposed to a solution containing antibodies that may bind to the antigen; and combinatorial synthesis of chemical compounds in which a chemical substrate is linked to the wells of the microplate.

A microplate having wells of any commonly-employed shape may be employed. It is not necessary that the pestle be fitted to the shape of the well; however, the pestle should displace sufficient reagent solution to ensure that the surfaces of the well to which a substance involved in the reaction is immobilized are covered by the reagent solution.

It is preferable that the use of the pestle not be accompanied by the formation of bubbles in the reagent solution. For this reason, it is preferable that the pestle have a smooth surface and that any edges thereof be sharp, as roughened edges may contribute to bubble formation.

Furthermore, the pestle should be made of materials that do not interact with the reagents employed in the reaction to be carried out in the well. For example, when DNA, RNA, or proteins are involved in the reaction, the pestle should be made of polypropylene or like materials that exhibit minimal non-specific absorption of nucleotides and polypeptides. It is preferable that the pestle be made of relatively hard materials that do not exhibit bending, twisting, deforming, or the like during use, and which are suitable for precision plastic molding.

Further qualities of the pestle will depend on the characteristics of the reaction to be carried out and the reagents to be employed. For example, when the pestle is to be used in cDNA synthesis reactions, it is preferable that the material of which the pestle is made be stable at temperatures of 37-45° C., while if cDNA synthesis is to be followed by subsequent rounds of polymerase chain reaction, it is preferable that the pestle be stable at temperatures up to 95° C. In either case, it is preferable that the pestle be of a material that can be made DNAse and RNAse free. Furthermore, when an assay is to be carried out involving fluorescence, as in real-time PCR, it is preferable that the pestle be made transparent.

Finally, it is preferable that the pestle be provided with a laterally extending portion which covers the top of the well so as to prevent evaporation of the reagent solution during the reaction process.

The method will next be explained with reference to preferred embodiments. These only exemplify specific applications of the method of the present invention and are not to be construed as limiting in any way.

Embodiment 1 cDNA Synthesis From Synthetic mRNA

An oligo(dT)-immobilized microplate, known commercially as a GenePlate®, containing oligo(dT) covalently immobilized in the area of each well that would be covered by 80 µL of liquid (the "80 µL area"), was employed to produce cDNA from synthetic mRNA in the following manner. 100 µL of synthetic RNA34, which contains polyA$_{40}$ sequences, was suspended in a lysis buffer. Such lysis buffers are known in the art; in a preferred embodiment, the lysis buffer comprises detergent (for example, 0.5% N-Lauroylsarcosine and 0.1% IGEPAL CA-630), a salt (for example, 4×SSC (0.6 M NaCl, 60 mM sodium citrate, pH 7.0)), a chelating agent (for example, 0.1-5 mM EDTA), a pH buffer (for example, 10 mM Tris HCl, pH 7.4), 1.791 M guanidine thiocyanate, RNAse inactivating agents (for example, proteinase K or 2-mercaptoethanol), tRNA (included in order to inhibit non-specific absorption of blood-derived DNA and RNA to filter plates), and exogenous DNA (for example, 10 mg/ml of sonicated salmon sperm DNA, added in order to inhibit non-specific absorption of blood-derived DNA and RNA to filter plates). Use of such a lysis buffer is not required to produce cDNA from synthetic mRNA as in the present embodiment; however, in order to maintain the same conditions that would be present if the mIRNA were obtained from a cell lysate, the lysis buffer was employed. The mRNA solution was applied to each well of the GenePlate so as to cover the 80 µL area.

Figure 2:
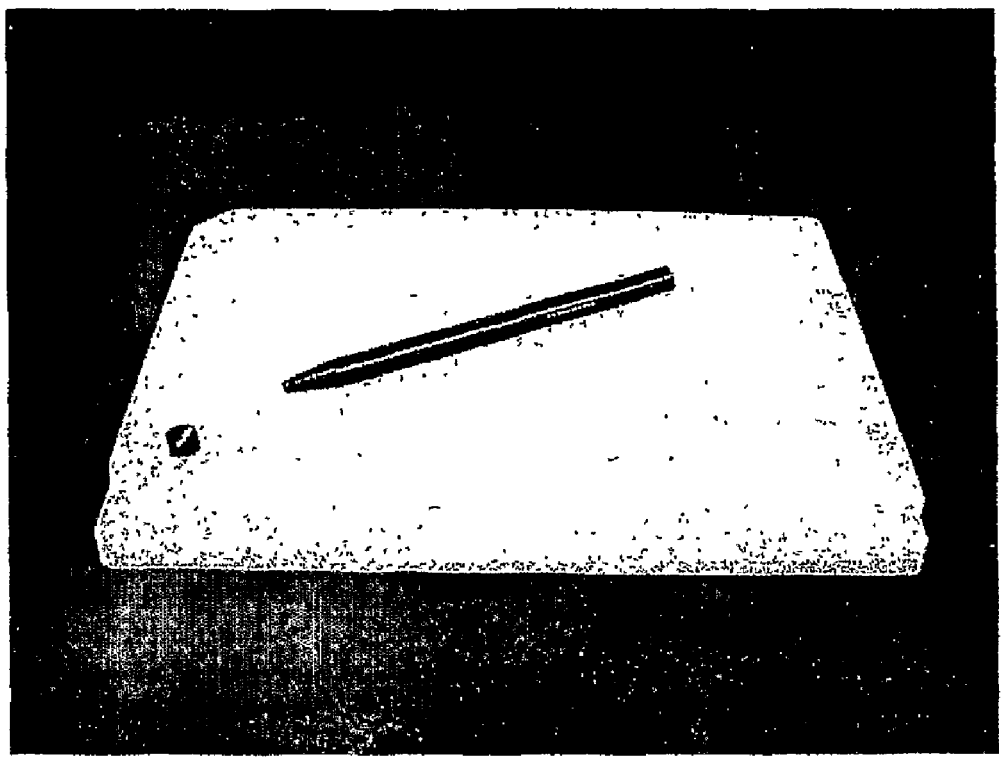
FIG. 2 shows a microplate and pestle suitable for use in an embodiment of the present invention.
Figure 3:
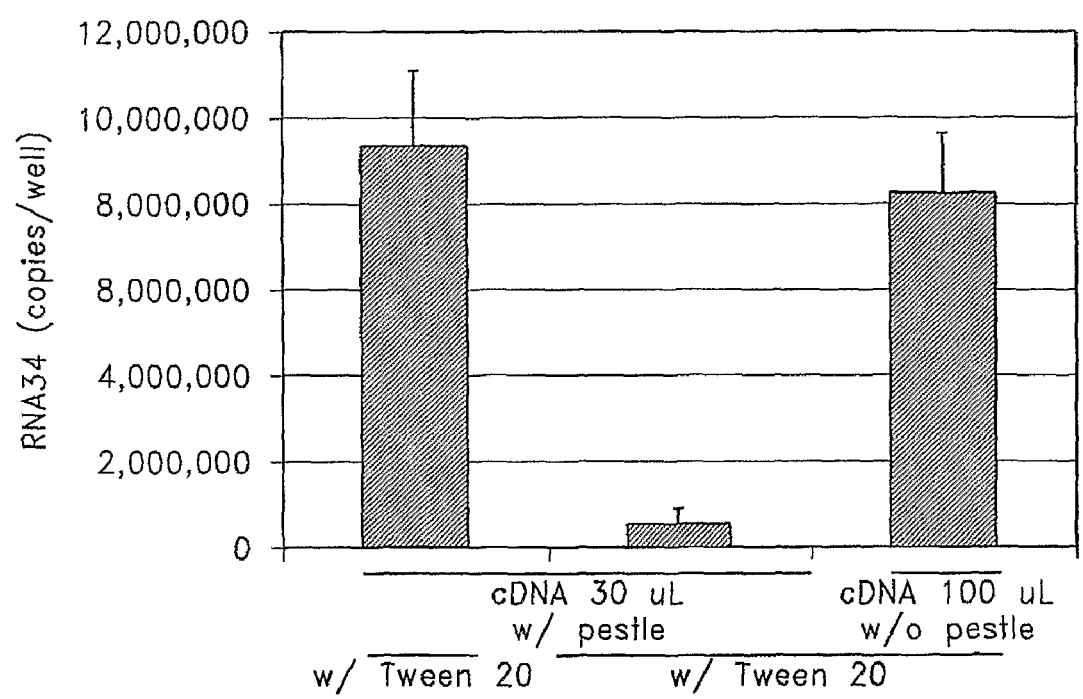
FIG. 3 shows the results of the generation of cDNA from RNA34 mRNA captured on a microplate in accordance with an embodiment of the present invention.

After overnight incubation at 4° C., unhybridized RNA34 was removed by washing each well with 100 µL of Lysis Buffer 3 times, followed by 150 µL of Wash Buffer 3 times. Subsequently, as shown in schematic view in FIG. 1, approximately 30 mL of cDNA synthesis buffer was placed in each well, after which a pestle was inserted into the well to wet a larger surface area (approximately the 80 µL area) with this volume of solution. FIG. 2 shows the actual pestle and GenePlate used for experiments. Pestles were purchased from Nalge Nunc International (Product # 749521-0590). Although the pestles did not perfectly fit each well, 25-30 µL of solution covered the entire well surface. Then cDNA was synthesized in each well at 37° C. for 2 hours, and 4 µL of cDNA was used for TaqMan real time PCR to quantitate RNA34. The y-axis in FIG. 3 shows the total RNA 34 recovered from total volume of cDNA, and each column and bar represent the mean and standard deviation from triplicate determinations. The third column shows the total RNA 34 recovered from 100 µL of cDNA. The second column shows the results of 30 µL of cDNA with pestle. In order to minimize nonspecific absorption of RNA and enzyme to pestles, Tween 20 was included in the cDNA synthesis solution. Before this experiment, it was confirmed that Tween 20 did not affect cDNA synthesis. Interestingly, as shown in FIG. 3, although the results using the pestle without Tween 20 were poor, the total recovered RNA 34 from 30 µL of cDNA with pestle and Tween 20 was equal to that of the positive control (column 3)

In converting all of the captured mRNA to cDNA in this embodiment, rather than employing the 80 µL of cDNA synthesis buffer that would ordinarily be required, only approximately 30 µL of solution was employed. It is also possible to employ a pestle in the mRNA hybridization step; this is particularly desirable when only small amounts of mRNA are obtainable for the reaction.

Embodiment 2

Combinatorial Chemistry Synthesis

In another embodiment of the invention, the method may be applied to solid-phase combinatorial synthesis. Such methods have been known since the 1960's. In this embodiment, the microplate functions as a cross-linked, insoluble polymeric material that is inert to the conditions of synthesis. A solid phase is linked thereto via a linker; examples thereof include carboxamide linkers such as methylbenzhydrylamine, an alcohol linker such as those based on the tetrahydropropanyl protecting group or trityl group, amine linkers, or traceless linkers such as silyl linkers. The solid phase linked to the microplate in each well, such as the initial monomer of an oligomeric molecule, is brought into successive contact with a solution of specific monomers in a randomized fashion to produce a set of unique oligomeric products in the wells of the microplate. As these reagents can be expensive, the use of a pestle that does not interfere with the process of the reaction allows a small volume of reagent solution to come into contact with a large surface area of each well, thus maximizing the opportunity for the reagents to react with the immobilized solid phase.

In an embodiment, approximately 30 µL of a solution containing a reagent to be added to the solid phase is introduced into a well, the 80 µL area of which has the solid phase of the reaction immobilized thereon. A pestle is thereafter introduced into the well, displacing reagent solution so that the surface area of the reagent solution is in contact with an increased portion of the well onto which the solid phase is immobilized. The reaction is then allowed to proceed. By repeating this process as desired, it is possible to produce the same amount of multimeric chemical molecules that would be produced if 80 µL of reagent solution were employed in each reaction, while employing less than half of that amount of reagent volume in actuality.

Embodiment 3

Enzyme-Linked Immunosorbent Assay

In another embodiment of the invention, the method may be applied to enzyme-linked immunosorbent assays (ELISAs). In these assays, an antigen of interest is immobilized on a substrate, typically the well of a microplate. Next, a liquid suspected of containing antibodies to the antigen, such as serum from a patient, is placed in the well. If the liquid contains such antibodies, those antibodies will bind to the antigens on the plate. Then, a second antibody, typically an anti-human immunoglobulin coupled to an enzyme is introduced to the well. This second antibody binds to the first antibody, if present. Finally, a chromogen or substrate which changes color when cleaved by the enzyme attached to the second antibody is introduced. The signal strength of this chromogen will be improved as more of the immobilized antigens participate in the reactions generating the signal. However, it is desirable to economize on the expensive or scarce (in the case of patient serum) reagents employed in this assay, and thus the method of the present embodiment is employed. The use of a pestle that does not interfere with the process of the reaction allows a small volume of reagent solution to come into contact with a large surface area of each well, thus maximizing the opportunity for the reagents to react with the immobilized antigens.

In an embodiment, approximately 30 µL of a solution containing a reagent to react with the immobilized antigen or antigen-antibody complex is introduced into a well, the 80 µL area of which has antigen immobilized thereon. A pestle is thereafter introduced into the well, displacing reagent solution so that the surface area of the reagent solution is in contact with an increased portion of the well onto which the antigen is immobilized. The reaction is then allowed to proceed. By use of the pestle in each step involving an expensive or scarce reagent, it is possible to produce the same signal strength that would be produced if 80 µL of reagent solution were employed in each reaction, while employing less than half of that amount of reagent volume in actuality.

What is claimed is:

1. A method of conducting a reaction in the wells of a microplate having a substance participating in the reaction immobilized onto a portion of a well thereof, comprising:
    transferring a volume of a solution of reagents for the reaction into the well, said volume being insufficient to cover the portion of the well onto which the substance is immobilized;
    inserting a pestle into the well, thereby increasing the surface area of the solution of reagents in contact with the portion of the well onto which the substance is immobilized; and
    conducting the reaction.

2. The method of claim 1, wherein the portion of the well onto which the substance is immobilized corresponds to more than half of the surface of the well.

3. The method of claim 1, wherein the portion of the well onto which the substance is immobilized corresponds to the portion covered when approximately 80 µl of reagents are transferred to the well.

4. The method of claim 3, wherein the volume of the solution of reagents is 30 µl or less.

5. The method of claim 2, wherein the substance is an oligonucleotide.

6. The method of claim 5, wherein the oligonucleotide is oligo d(T).

7. The method of claim 1, wherein the substance is an antigen.

8. The method of claim 1, wherein the reaction is a cDNA synthesis reaction.

9. The method of claim 8, wherein the reagents comprise a detergent.

10. The method of claim 9, wherein the detergent is polyoxyethylene (20) sorbitan monolaurate (Tween 20).

11. The method of claim 1, wherein the reaction is part of an enzyme-linked immunosorbent assay.

12. The method of claim 1, wherein the reaction is a solid-phase chemical synthesis reaction.

13. A method of synthesizing cDNA, comprising:
    transferring a mRNA-containing solution to a well of a microplate, at least a portion of said well having oligo d(T) immobilized thereto;
    hybridizing the mRNA to the oligo d(T);
    washing the well to remove unbound mRNA;
    transferring a volume of a solution of reagents for synthesizing cDNA into the well, said volume being insufficient to cover the portion of the well onto which the oligo d(T) is immobilized;
    inserting a pestle into the well, thereby increasing the surface area of the solution of reagents in contact with the portion of the well onto which the oligo d(T) is immobilized; and
    conducting a cDNA polymerization reaction.

14. The method of claim 13, wherein the hybridizing step includes inserting a pestle into the well, so as to increase the surface area of the mRNA-containing solution in contact with the portion of the well onto which the oligo d(T) is immobilized.

* * * * *

UNITED STATES PATENT AND TRADEMARK OFFICE
CERTIFICATE OF CORRECTION

| | |
|---|---|
| PATENT NO. | : 7,816,081 B2 |
| APPLICATION NO. | : 11/913052 |
| DATED | : October 19, 2010 |
| INVENTOR(S) | : Masato Mitsuhashi and Mieko Ogura |

It is certified that error appears in the above-identified patent and that said Letters Patent is hereby corrected as shown below:

On page 1, column 1, Item 65, under Prior Publication Data, insert --Related U.S. Application Data. This application is a 371 of PCT/US06/16321, filed on April 28, 2006, which claims benefit of U.S. Provisional application No. 60/675,751, filed on Apr. 28, 2005.-- therefor.

Title page, column 2, under Other Publications line 10, delete "TNT- ]" and insert --TNF-α--, therefor.

At sheet 3 of 3, FIG. 3, line 4, delete "8,000,000" and insert --6,000,000--, therefor.

At column 4, line 16, delete "mIRNA" and insert --mRNA--, therefor.

At column 4, line 45, after "3)" and insert --.--, therefor.

Signed and Sealed this
Fourth Day of October, 2011

David J. Kappos
*Director of the United States Patent and Trademark Office*